United States Patent [19]

Agnello

[11] Patent Number: 6,030,773

[45] Date of Patent: Feb. 29, 2000

[54] CHEMILUMINESCENT ASSAY FOR DSDNA ANTIBODIES

[76] Inventor: Vincent Agnello, 11 French Rd., Weston, Mass. 02193

[21] Appl. No.: 07/911,667

[22] Filed: Jul. 8, 1992

[51] Int. Cl.[7] .............................. C12Q 1/68; G01N 33/53
[52] U.S. Cl. .................................. 435/6; 435/7.1
[58] Field of Search ................. 436/508; 435/6, 435/7.1

[56] References Cited

U.S. PATENT DOCUMENTS 4,391,904  7/1983  Litman et al. .............. 435/7

OTHER PUBLICATIONS

J. Lab.Clin. Med. 97:842–853 (1981) Pope. R.M. et al "IgG Rheumatoid factor: analysis . . . ".

J. Immunol. Methods 132:91–101 (1990) Emlem. W. et al. "A new ELISA for detection of ds–DNA . . . ".

Pollard–Knight, J. Meth Cell. Mol. Biol. 2:113–132 (1990) "Current methods in nonradioactive . . . ".

Pope et al., J. Lab. Clin. Med. 97:842–853 (1981) "IgG Rheumatoid factor: ".

Emlen et al., J. Immun. Meth. 132:91–101 (1990) "A new ELISA for the detection . . . ".

*Primary Examiner*—Eggerton A. Campbell
*Attorney, Agent, or Firm*—Robert J. Schiller

[57] ABSTRACT

An assay for systemic lupus erythematosus based upon capture of the anti-dsDNA portion of IgG in a human serum specimen by the Fc part of a molecule using solid phase immobilized F(ab')2 fragment of anti-human IgG specific for Fc, the captured IgG being then incubated with a synthetic dsDNA tagged with a moiety from which a signal proportional to the quantity of said synthetic dsDNA can be elicited. Upon eliciting a signal from the moiety, the amount of antibody to dsDNA can be quantified, providing diagnostic and prognostic information regarding the disease.

7 Claims, No Drawings

CHEMILUMINESCENT ASSAY FOR DSDNA ANTIBODIES

This invention relates to biochemical assays, and more particularly to assays for antibodies to double-stranded nucleic acids.

Polymeric chains of deoxyribonucleic acid (DNA), being integral parts of the nuclear material of biological cells in double-stranded form (dsDNA), do not ordinarily stimulate the immune system to form antibodies. At least one disease, systemic lupus erythematosus, is however characterized by apparent abnormalities of the immune system that causes antibodies to be formed to dsDNA with fatal results. Antibodies to dsDNA occur almost exclusively in systemic lupus erythematosus and assay for such antibodies is one of the laboratory tests used in the diagnosis and determination of the prognosis of the disease.

Heretofore, measurement of anti-dsDNA antibody has typically been accomplished by using a radioactive immunoassay in which a complex formed between the antibody and antigen is labelled with a radioactive material, and a measurement of the radioactivity of the resulting product is measured as with a Geiger counter, photochemically or the like. The radioactive materials used in such assays may pose a significant danger, and where they have limited half-lives, frequent calibration is necessary. Alternatively one can use an enzyme-linked immunoabsorbent assay employing an enzyme linked to a molecule specific to an antibody bound to an antigen on a solid phase, e.g. peroxidase phosphate. A chromogenic substrate is added to generate a colored end product in the presence of the enzyme portion of the ligand. While such an assay is stable, it is far less sensitive than radioimmunoassays. Unfortunately also, rheumatoid factors tend to react with the Fc portion of the human IgG and thus may seriously interfere with the assay.

The known Crithidia assay does assay for true dsDNA but, being at best semi-quantitative, cannot follow the activity of the disease.

A principal object of the present invention is therefore to provide an assay for anti-dsDNA antibody, which assay is stable, yet highly sensitive, and uses no materials that pose a significant health threat to the assayer. Yet other objects of the present invention are to provide such an assay that, being linearly quantitative, has particular utility in clinical medicine; and to provide such an assay that measures only IgG antibody that relates to the disease activity.

Generally these and other objects of the present invention are realized by an assay that incorporates a capture system for double stranded IgG antibody and thereby allows measurement of the antibody only. The assay captures the anti-dsDNA portion of IgG in a human serum specimen by the Fc part of a molecule using solid phase immobilized F(ab')2 fragment of anti-human IgG specific for Fc, the captured IgG being then incubated with a synthetic dsDNA tagged with a moiety from which a signal proportional to the quantity of said synthetic dsDNA can be elicited. Upon eliciting a signal from the moiety, one may quantify the amount of antibody to dsDNA.

More specifically, a preferred embodiment of the present invention involves immobilizing F(ab')2 fragment of anti-human IgG antibody, such as goat anti-human IgG antibody, specific for the Fc part of a molecule, on an inert substrate or immunoadsorbent. The present invention employs F(ab')2 to avoid rheumatoid factors that would otherwise interfere with the assay because the latter tend to react with the Fc portion of the IgG. A dilution of a human patient serum specimen believed to contain an anti-dsDNA portion of IgG, is then permitted to contact the coated substrate under conditions and for a period of time sufficient for a proportion of the patient IgG to become bound by reaction with the animal anti-IgG antibody. Synthetic double-stranded DNA is labelled, for example, with digoxigenin inasmuch as the use of the latter must result in dsDNA antibody that does not have a single-stranded or denatured component. The digoxigenin is added to the serum, again under conditions and for a time sufficient to bind to any anti-DNA antibodies which may be present in the serum. The extent to which the labelled dsDNA is bound to the solid phase immunoadsorbent is determined by adding an anti-digoxigenin antibody coupled to alkaline phosphatase. The amount of alkaline phosphatase present is measured by the further addition of a chemiluminescent substrate and the resulting luminescence due to reaction of the alkaline phosphatase with the substrate, if any, is measured with a luminometer. The use of chemiluminescence as a tag or label provides sufficient sensitivity to provide excellent quantitative determination. The levels of luminescence obtained are compared to standard levels provided by the similar reaction of standard quantities of anti-dsDNA antibodies and expressed as U/mL, thereby relating the amount of bound labelled synthetic double-stranded DNA detected to a predetermined quantitative relationship between the amount of labelled double-stranded DNA and the amount of animal anti-human IgG antibody to determine the amount of human IgG in the serum.

Pure double-stranded DNA molecules are provided for use in the anti-dsDNA assay. The synthesis of the DNA from a single-stranded DNA M13 phage molecule is initiated with random primers and carried out with dATP, dGTP, dCTP, dTTP and digoxigenin-labelled deoxyuridine-triphosphate in the presence of sequenase enzyme, as will be described hereinafter in detail.

Not all antibodies present in individuals have the same affinity or avidity for the dsDNA antigen as does the standard antibody preparation. Differences in avidity between the standard and the individual patient samples results in non-linear dose response curves. Because of this non-linearity, a two-fold dilution of a sample may not result in a U/mL value that is one-half of the undiluted sample result. The binding activity, however, of a patient sample will be reproducible and consistent at a given dilution. For this reason, all samples with u/mL over a 150 U standard are diluted as little as possible for reanalysis, and some patients may need to always be analyzed at a set dilution so that sequential results over time can be compared.

Molecular biology techniques are used to generate pure, double-stranded DNA molecules for use in the anti-dsDNA assay. The DNA is typically synthesized from single-stranded DNA M13 circular phage molecules (0.2 $\mu g/\mu L$, USB #70704). This DNA synthesis is initiated with random primers and carried out with dATP, dGTP, dCTP, dTTP and digoxigenin-labeled deoxyuridine-triphosphate (duTP) (Boeringer Mannheim #1093088), in the presence of sequenase enzyme, a DNA polymerase (USB #707775). Digoxigenin is a known steroid that occurs naturally in digitalis plants.

All pipet tips used for this procedure must be autoclaved and should not be touched without gloved hands.

An example of the DNA labeling/synthesis procedure is as follows: An M13 sequencing forward primer (24 Mer), 20 $\mu M$ (New England Biolabs #1224), is annealed to the M13 DNA by pipetting 30 $\mu L$ of 20 $\mu M$ forward primer and 120 $\mu L$ of 5×sequenase buffer (USB #70765) into a Perkin Elmer reaction tube. A mixture is formed by pipetting 5 $\mu L$ of the annealed M13 DNA and 10 μL of the single-stranded DNA M13 circular phage molecules (0.2 μg/μL) into a reaction tube where they are mixed, spun in a centrifuge for about five seconds or less, and placed into a Perkin-Elmer DNA Thermal Cycler machine. The mixture is heated in the machine to 65° C. over two minutes, such temperature held for five minutes, and then allowed to cool slowly to about 4° C. over fifteen minutes. When cooled, the tube is removed from the machine and placed immediately on ice. While the primer is annealing, a labeling cocktail mixture is prepared by adding 5.50 μL each of 10 μM adenine stock solution, guanine stock solution, and cytosine stock solution, 3.575 μL of 10 μM thymidine stock solution, 19.250 μL of 1 μM digoxigenin labeled duTP stock solution, 27.50 μL of 0.1M dithiothreitol, (USB (#70726), and 15.675 μL of distilled water, to a total of 82.50 μL.

To an empty reaction tube, 56 μL of the enzyme dilution buffer is added. The sequenase enzyme is removed from the freezer where it should be kept, 8 μL thereof is added to the enzyme dilution buffer, and 55 μL of this mixture is added to the labelling cocktail mixture. 5 μL of this prepared labeling cocktail/sequenase solution is added to the iced tube containing M13 DNA with annealed primer, mixed well and pulse spun. The tube is placed into a "floater" in a 37° C. water bath, incubated for 45 minutes, removed and placed on ice and immediately 2 μL 0.5M EDTA is added to stop any further reaction. A kit for labeling reactions of 10 ng-3 μg DNA with digoxigenin-labeled deoxyuridine-triphosphate is commercially available from Boehringer-Mannheim Chemicals, Indianapolis, Indiana, together with instructions for carrying out the procedure.

Known agarose gel electrophoresis and modified Southern blot procedures are preferably used to check that the molecular weight of the newly prepare DNA and the efficiency of the digoxigenin labeling are correct. Ultraviolet spectrophotometry is also preferably employed to adjust the concentration of the DNA to lots previously prepared and to ensure its purity.

The present invention preferably involves the preparation of an appropriate solid-phase support for anti-human IgG antibody. First an 0.05 M Tris buffer, ph 9.5 is made by weighing out 5.789 gm Tris base (Sigma Chemical Co., St. Louis. Mo., T-1503) and 0.3346 gm Tris acid (Sigma, T-3253). These materials are added to a 1.0 L graduated cylinder, Q.S. to 1.0 L with distilled water and the pH checked to ensure that it is at 9.5. This buffer is stored at 4° C. where it will remain stable for about three months. Preferably the day before the assay is to be performed, a 2.5 uG/mL solution of the capture antibody, preferably an animal anti-human IgG antibody, such as goat anti-human IgG (Fc specific Jackson #109-006-008 supplied at 1.1 mg/mL), is prepared by adding 25 μL of the stock F(ab)'2 anti-human IgG (1.1 mg/mL to 11 mL of the 0.05 M Tris coating buffer (1:500 dilution). Using a Titerteck 8 channel pipet, 100 μL of the anti-IgG/coating buffer is added to each well of a 96-well black, microfluor, microtiter plate. The plate is covered with a plastic plate sealer and incubated for 6 hours at room temperature.

The hybridization procedure to carry out the assay of the present invention is described in a document entitled, Genius™, Nonradioactive DNA Labeling and Detection Kit, published by Boehringer-Mannheim, September, 1988, the contents of which are incorporated herein by reference.

Specifically, a blocking buffer is prepared by adding 250 mg bovine serum albumin (Sigma A-2153) to 25 mL of the 0.05 M Tris buffer and mixing gently to ensure complete solubilization of the bovine serum albumin in the buffer. The coating solution is now flicked out of the microtiter plate into a sink, the plate is inverted and the tops of the wells blotted with paper towels to dry thoroughly each well. Then, 200 μL of blocking buffer is added to each well, the plate is covered with a plastic plate sealer and incubated at 4° C. overnight.

Preparatory to performing the assay of the present invention, fresh solutions of washing and sample dilution buffers are prepared by as follows.

A 0.01M phosphate buffer solution −10× (hereinafter PBS) is prepared by weighing out the following:

85.0 g. NaCl (Sigma, S-9625)

11.5 g. $Na_2HPO_4$ (Baker Chemical Co., Phillipsburg, N.J. 3828-5 anhydrous)

2.0 g. KCl (Sigma, P-4504)

2.0 g. $KH_2PO_4$ (Sigma, P-5379)

1.0 g. Thimerosal (Sigma, T-5125)

The foregoing materials are placed in a 1.0 L graduated cylinder, distilled water is added to Q.S. to 1.0 L, and the solution mixed. This stock solution of phosphate buffer solution or PBS should be at pH 6.8.

A PBS/TWEEN buffer is prepared by mixing 100 mL of 10× PBS solution with 900 mL of distilled water. 0.5 mL of Tween (0.01M PBS/0.05% polyoxyethylene-sorbitan monolaureate, (Sigma, P-1379)) is added and mixed gently to avoid foaming.

A PBS wash buffer (0.01M PBS) is prepared by mixing 45 mL of stock 10× PBS solution with 450 mL of distilled water.

A sample dilution buffer (0.01M PBS/0.05% Tween/ 0.02% bovine serum albumin (hereinafter BSA)) is prepared by mixing 5.0 mL with 45 mL of distilled water and then adding 50 μL of Tween and 10 mg BSA (Sigma, A-2135).

Standards and controls are prepared as follows from a stock serum sample taken from a patient with a known high concentration of DNA antibodies:

A "high" standard is prepared from by dilution in diluting buffer to a standardized IgG concentration of 825 mg/mL, as by mixing an appropriate amounts of μL of the standard or stock serum in the diluting buffer.

A "medium" standard, prepared from the "high" standard to be 60% of the value of the latter, is made by mixing 600 μL of high standard with 400 μL of diluting buffer.

Dilutions are prepared for all controls and standards by adding 10 μL of serum of each to 490 μL of sample dilution buffer (BSA) in respective test tubes. For patients from a previous run which proved to be strongly positive above the highest standard value, two dilutions are made, one being a mixture of 50 μL aliquots of normal Lit serum and the patient serum, the other being a mixture of 150 μL normal Lit serum and 50 μL of the patient serum. To two 490 μL aliquots of the sample dilution buffer, 10 μL are added from each of these dilutions to provide 1:50 dilutions. Similarly, 1:50 dilutions are prepared for each patient sample to be assayed.

The incubated plate, prepared as hereinbefore described is placed on a platewasher and the blocking buffer is aspirated from it. The aspirated plate is then washed with PBS/Tween buffer a total of six times. The plate is then removed from the washer, blotted with paper towels so that the wells are completely free of buffer. For each standard, control and patient sample, 100 μL of each is added to respective wells in the plate, and 100 μL of the sample dilution buffer is added to duplicate blank wells. The plate is then covered with a plate sealer and incubated in a humid chamber at 37° C. for 1 ½ hours. Just prior to the end of the incubation period a 1:500 dilution is made of the dsDNA-digoxigenin solution by adding 24 µL of stock DNA solution to 12 mL of diluting buffer (0.1 µL/mL) At the end of the incubation period, the diluted sample solution are aspirated and the plate is washed with PBS/Tween buffer. The plate is then blotted and tapped to dry completely.

With a channel pipet, 100 µL aliquots of the diluted dsDNA-digoxigenin solution are added to each well of the plate which is then covered with a plate sealer and again incubated in a humid chamber at 37° C. for 1 ½ hours. At the end of this incubation time, the diluted dsDNA-digoxigenin solution is aspirated from the plate and the plate washed with PBS/Tween buffer. The plate is then blotted and tapped to dry completely.

Just before the end of the incubation period, a 1:500 dilution is made of the stock anti-digoxigenin solution in sample diluent, and 100 µL aliquots of this dilution are added to each well. Again the plate is covered with a plate sealer and again incubated for a third time in a humid chamber at 37° C. for 1 ½ hours. At the end of this third incubation, the diluted stock anti-digoxigenin solution is aspirated from the plate, the plate washed with PBS/Tween buffer and the latter replace then with PBS without Tween. The wash lines are primed to ensure complete removal of the PBS/Tween buffer, the plate washed with PBS without Tween, blotted and tapped to dry completely.

During the third incubation period at least 12 mL of the chemiluminescence alkaline phosphatase substrate, such as Lumiphos 530, is removed from refrigeration, allowed to come to room temperature, and 100 µL aliquots thereof added to each dried well after the incubation period. Detection of the digoxigenin-labeled probe is preferably accomplished with an antibody-enzyme conjugate such as anti-digoxigenin-alkaline phosphatase. The latter may be visualized by known enzyme-linked color reactions but in the present invention, is preferably accomplished by chemiluminescent detection. To this end, the support carrying the hybridized probe and bound antibody conjugate, is reacted with a known chemiluminescent substrate for alkaline phosphatase, such as a 1,2-dioxetane commercially available in a solution known as Lumi-Phos™ 530 from Boehringer Mannheim. The reaction protocol can be carried out as described in a publication entitled Lumi-Phos™ 530 available from Lumigen, Inc., a division of Boehringer Mannheim Chemicals. In order to detect the chemiluminescence, it is preferred to use a luminometer such as an Amerlite™ chemiluminescent detector available from Eastman Kodak Co., Rochester, N.Y.

Immediately following the addition of the chemiluminescent substrate, the plate is placed into a luminometer and run according to the instructions for that particular device, providing readings for each well. The plate is left in the machine and at the end of a 45 minute incubation period, the machine instructed to reread the wells, providing a second set of data. To determine if the reaction is at an endpoint, the initial and final readings of the "medium" and "high" standards are compared and should be within 5 units for each sample. Preferably, the machine will provide curve fitting statistics and the mean value for each set of replicate wells for all standards, controls and patients. Normal individuals with have 15 U/mL of dsDNA antibody.

A run is acceptable on the Amerlite detector if all of the following criteria are met: (1) the curve fit factor is <10.0; the light index is >10.0; and the % difference for each point in the standard curve provided by the luminometer is <5.0, (2) for the controls, the "medium" and "high" controls at the beginning and end of the batch of samples are each within 5 units; replicate wells should have CVs less than 10%; and the mean values of all controls must be within their accepted duality control limits, and (3) for the patient samples, replicate wells should have CVs less than 10%; and values above the highest standard must be repeated on a subsequent run to obtain a value within the standard curve.

For patients that are run in dilutions of normal serum, the values may be calculated as follows:

For the 1:2 volume dilution:.
Reported value in U/mL=A×(B+C)/B
where
A=U/mL from the standard curve;
B=IgG level in the patient serum; and
C=IgG level in the normal control serum.
For the 1:4 volume dilution:
Reported value=A+(B+3C)/B For all patient samples above the top standard, the next run should be repeated with additional dilutions. It will be appreciated that readings above the top standard are diagnostic of a diseased condition characterized by antibodies formed to dsDNA, most probably systemic lupus erythematosus. It is suggested that as such disease progresses, the extent to which the assay increases beyond the normal U/ml of dsDNA antibody is indicative of the activity of the disease.

Since certain changes may be made in the above method without departing from the scope of the invention herein involved, it is intended that all matter contained in the above description or shown in the accompanying drawings shall be interpreted in an illustrative and not in a limiting sense.

What is claim is:

1. A method of assaying for antibodies to human double-stranded DNA in a liquid, human-serum specimen, said method comprising the steps of:

forming a first incubation mixture of said specimen and a solid phase immunoadsorbent having immobilized thereon animal anti-human IgG antibody including F(ab')2 fragment specific for IgG Fc;

incubating said first mixture under conditions and for a period of time sufficient for Fc in human IgG in said specimen to become bound by said F(ab')2 fragment in said animal anti-IgG antibody;

forming a second incubation mixture of said first mixture and digoxigenin-labelled synthetic double-stranded DNA under such conditions and for a period of time sufficient to bind to said immunoadsorbent any anti-DNA antibodies which may be present in the serum so as to form a double-stranded DNA antibody that has substantially no single stranded or denatured components;

detecting the amount of digoxigenin labelled synthetic double-stranded DNA bound to said immunoadsorbent; and relating the amount of bound labelled synthetic double-stranded DNA detected to a predetermined quantitative relationship between the amount of labelled double-stranded DNA and the amount of animal anti-human IgG antibody to determine the amount of human IgG in said specimen.

2. A method of assaying for antibodies to human double-stranded DNA in a human serum specimen, said method comprising the steps of:

capturing the anti-double-stranded DNA portion of IgG in said human serum specimen by the Fc part of a molecule using solid phase immobilized F(ab')2 fragment of anti-human IgG specific for Fc;

incubating the captured IgG with synthetic double-stranded DNA tagged with a moiety from which a signal proportional to the quantity of said synthetic double-stranded DNA can be elicited;

eliciting said signal; and quantifying the amount of antibody to double-stranded DNA in accordance with the elicited signal.

3. A method as defined in claim 2 wherein said captured IgG is incubated with synthetic double-stranded DNA tagged with alkaline phosphatase, and said elicited signal is proportional to the quantity of alkaline phosphatase tagging said synthetic double-stranded DNA.

4. A method as defined in claim 3 including the step of incubating comprises:

adding chemiluminescent substrate to said antibody, and measuring any resulting luminescence from the reaction of said substrate with said phosphatase.

5. A method as defined in claim 2 wherein said step of capturing is effected by:

coating animal anti-human IgG antibody onto an inert substrate;

contacting the coated substrate with a dilution of said serum so that a proportion of the patient IgG becomes bound by reaction with said animal anti-IgG antibody; and labelling synthetic double-stranded DNA with digoxigenin and is added the labelled DNA to said serum to bind to any anti-DNA antibodies which may be present in the serum.

6. A method as defined in claim 5 including the step of incubating comprises:

contacting said labelled DNA with an anti-digoxigenin antibody coupled to alkaline phosphatase, adding a chemiluminescent substrate to said anti-digoxigenin antibody, and measuring any resulting luminescence from the reaction of said substrate with said phosphatas.

7. A method as defined in claim 5 including the further step of comparing the measurement of said luminescence with predetermined standard levels.

* * * * *